US011458086B2

(12) United States Patent
Mama et al.

(10) Patent No.: US 11,458,086 B2
(45) Date of Patent: Oct. 4, 2022

(54) METHOD AND COMPOSITION

(71) Applicant: PERACHEM LIMITED, London (GB)

(72) Inventors: John Mama, London (GB); David Lewis, London (GB); Sarah Lucas, London (GB)

(73) Assignee: HSNF Limited, London (GB)

( * ) Notice: Subject to any disclaimer, the term of this patent is extended or adjusted under 35 U.S.C. 154(b) by 0 days.

(21) Appl. No.: 17/286,169

(22) PCT Filed: Oct. 16, 2019

(86) PCT No.: PCT/GB2019/052951
§ 371 (c)(1),
(2) Date: Apr. 16, 2021

(87) PCT Pub. No.: WO2020/079430
PCT Pub. Date: Apr. 23, 2020

(65) Prior Publication Data
US 2021/0378933 A1  Dec. 9, 2021

(30) Foreign Application Priority Data

Oct. 18, 2018 (GB) ..................... 1817000

(51) Int. Cl.
| *A61Q 5/10* | (2006.01) |
| *A61K 8/49* | (2006.01) |
| *A61K 8/34* | (2006.01) |
| *A61K 8/362* | (2006.01) |
| *A61K 8/42* | (2006.01) |
| *A61K 8/46* | (2006.01) |
| *A61Q 1/10* | (2006.01) |

(52) U.S. Cl.
CPC ............ *A61K 8/4946* (2013.01); *A61K 8/345* (2013.01); *A61K 8/362* (2013.01); *A61K 8/42* (2013.01); *A61K 8/466* (2013.01); *A61K 8/4973* (2013.01); *A61Q 1/10* (2013.01); *A61K 2800/4322* (2013.01); *A61K 2800/87* (2013.01)

(58) Field of Classification Search
CPC . A61Q 5/10; A61Q 5/065; A61K 8/34; A61K 2800/4322; A61K 8/345; A61K 8/362; A61K 2800/87

USPC ............................................... 8/405
See application file for complete search history.

(56) References Cited

U.S. PATENT DOCUMENTS

| 2002/0144356 A1* | 10/2002 | Kawai ..................... A61K 8/40 |
| | | 8/405 |
| 2003/0066141 A1* | 4/2003 | Oshika ................. A61K 8/345 |
| | | 8/408 |
| 2008/0102047 A1 | 5/2008 | Appel et al. |
| 2013/0276811 A1* | 10/2013 | Wood ...................... A61K 8/23 |
| | | 8/408 |
| 2015/0047131 A1* | 2/2015 | Hawkes .................. A61Q 5/10 |
| | | 8/405 |
| 2015/0068548 A1* | 3/2015 | Hawkes .................. A61K 8/42 |
| | | 8/405 |
| 2015/0086500 A1* | 3/2015 | Castro ..................... A61K 8/06 |
| | | 424/70.7 |
| 2016/0303014 A1* | 10/2016 | Grevalcuore ........... A61Q 5/04 |
| 2017/0354583 A1* | 12/2017 | Goutsis .................. A61Q 5/065 |

FOREIGN PATENT DOCUMENTS

| CN | 105362096 A | 3/2016 |
| EP | 3295923 A1 | 3/2018 |
| EP | 3342464 A1 | 7/2018 |
| FR | 3042115 A1 | 4/2017 |
| GB | 2259717 A | 3/1993 |
| GB | 2500999 A | 10/2013 |
| JP | 2008056607 A | 3/2008 |
| JP | 2011207865 A | 10/2011 |

OTHER PUBLICATIONS

PCT International Search Report and Written Opinion for International Application No. PCT/GB2019/052951, dated Dec. 19, 2019, 11 pages.
Great Britain Search Report for Application No. GB1817000.1, dated Apr. 1, 2019, 4 pages.

\* cited by examiner

*Primary Examiner* — Eisa B Elhilo
(74) *Attorney, Agent, or Firm* — Hoffman Warnick, LLC

(57) ABSTRACT

A method of colouring an eyebrow, the method comprising: (I) applying to the eyebrow a colouring composition comprising: (a) one or more dye compounds selected from Acid yellow (23), Food Red (17), Acid Blue (9) and Acid Green (25); (b) an organic acid; (c) an alkylene carbonate; (d) an alcohol; and (e) glycerol and/or urea.

8 Claims, No Drawings

METHOD AND COMPOSITION

The present invention relates to methods for colouring eyebrows and to compositions for use in the method.

The dyeing of eyebrows is becoming increasingly common for fashion or other purposes. As eyebrows are so prominent it is important to achieve consistent even colour, in a method that is mild to the skin.

It is also desirable to provide a colour which does not fade easily. In some instances, in which a user desires a "natural" result, it is also desirable to avoid staining of the skin between the hairs.

The present inventors have found a method of colouring eyebrows which provides excellent results.

According to a first aspect of the present invention there is provided a method of colouring an eyebrow, the method comprising:
(i) applying to the eyebrow a colouring composition comprising:
    (a) one or more dye compounds selected from Acid Yellow 23, Food Red 17, Acid Blue 9 and Acid Green 25;
    (b) an organic acid;
    (c) an alkylene carbonate;
    (d) an alcohol; and
    (e) glycerol and/or urea.

According to a second aspect of the present invention there is provided a colouring composition for colouring eyebrows comprising:
(a) one or more dye compounds selected from Acid Yellow 23, Food Red 17, Acid Blue 9 and Acid Green 25;
(b) an organic acid;
(c) an alkylene carbonate;
(d) an alcohol; and
(e) glycerol and/or urea.

Preferably the method of the first aspect involves contacting the material with a composition of the second aspect.

Preferred features of the first and second aspects will now be described.

The colouring composition comprises a dye selected from Acid Yellow 23, Food Red 17, Acid Blue 9 and Acid Green 25.

The Colour Index International is a standard classification system for dyes and pigments which contains historic, proprietary, generic names and generic numbers that have been applied to colours. It was first published in 1924 and has been updated and reprinted since. The $2^{nd}$ (1956), $3^{rd}$ (1971) and $4^{th}$ (2002) editions are jointly published and maintained by the Society of Dyers and Colourists (SDC) (UK) and American Association of Textile Chemists and Colourists (AATCC). The structures of the dye compounds shown in this specification are taken from the Colour Index International.

Acid Yellow 23 has the structure (A):

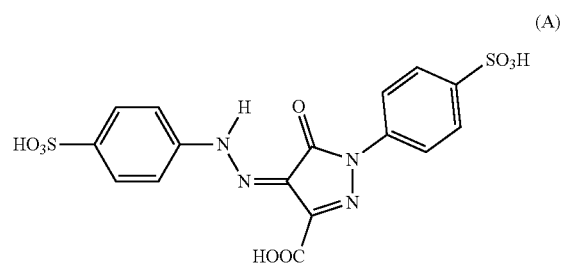 [SMILES: O=C(O)C1=NN(c2ccc(S(=O)(=O)O)cc2)C(=O)/C1=N\Nc1ccc(S(=O)(=O)O)cc1]

This compound is also know as Acid Tartrazine, FD&C Yellow 5 and Eurogran tartrazine.

Acid Blue 9 has the structure (B):

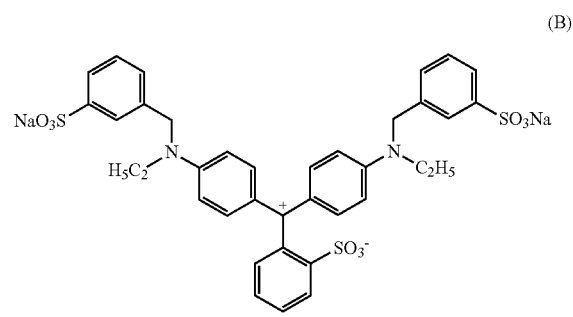

This compound is also know as Duracol Brilliant Blue FCF E133, CI Food Blue 2 and FD&C Blue 1.

Food Red 17 has the structure (C):

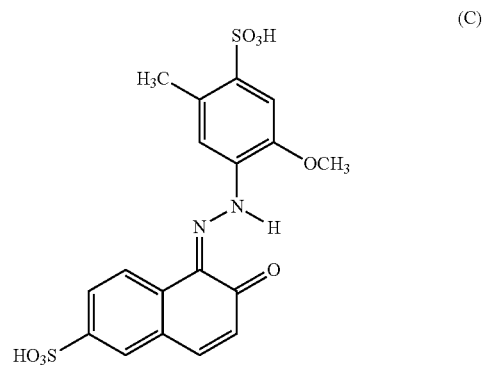 [SMILES: COc1cc(S(=O)(=O)O)c(C)cc1N/N=C1\C(=O)C=Cc2cc(S(=O)(=O)O)ccc21]

This compound is also known as FD&C Red 40.

Acid Green 25 has the structure (D):

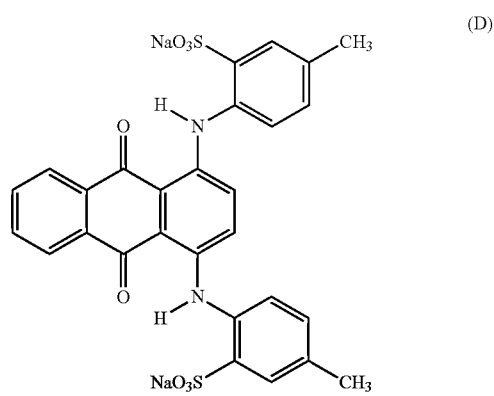

This compound is also known as D&C Green 5.

The colouring compositions of the present invention may include a mixture of two or more dye compounds. Mixtures of dyes may be combined in a specific ratio to achieve a desired colour or other visual effect.

The colouring composition preferably comprises at least 0.0001 wt % of the dye compound. Preferably it comprises at least 0.001 wt %, more preferably at least 0.01 wt %, suitably at least 0.05 wt %, preferably at least 0.1 wt %, for example at least 0.5 wt %.

The colouring composition suitably comprises up to 40 wt % of the dye compound, preferably up to 30 wt %, more preferably up to 25 wt %, suitably up to 20 wt %, preferably up to 15 wt %, more preferably up to 12 wt %, for example up to 10 wt %, up to 7 wt %, up to 5 wt % or up to 3 wt %.

Commonly the composition of the present invention comprises a mixture of two or more dye compounds. The above amounts refer to the total amounts of all dye compounds present in the composition.

Suitably dyes are present in the composition in a total amount of from 0.1 to 2.5 wt %, for example 0.25 to 2 wt % or 0.5 to 1.5 wt %.

Preferably the colouring composition of the present invention comprises less than 1 wt % oxidative dye compounds or precursors thereof.

Oxidative hair dyes are well known and the skilled person will recognise the types of compounds used. It will be appreciated that the precise nature of the coloured species present in the hair is often not clear since they are formed in situ by treatment of the hair with one or more precursor compositions (suitably containing an aromatic amine and a coupler compound) and an oxidising composition. Typically when hair is oxidatively dyed an aromatic amine composition and a coupler are mixed with a developer immediately before application to the hair. The developer is usually an oxidising composition containing for example hydrogen peroxide. The aromatic amine and coupler precursor compositions comprise small aromatic compounds which interact in the presence of the oxidising developer to form large aromatic conjugated species which are coloured. Although these compounds are referred to as "hair dyes", the resulting coloured species may more correctly be referred to as pigments since they are usually water insoluble.

By oxidative dye compounds or precursors thereto we mean to refer to the compounds formed during the oxidative dyeing process or the precursor aromatic amine or coupler compounds.

Preferably the colouring composition of the present invention comprises less than 0.1 wt % oxidative dye compounds or precursors thereof, preferably less than 0.01 wt %, more preferably less than 0.001 wt %, preferably less than 0.0001 wt %.

Preferably the composition does not comprise any oxidative dye compounds or precursors thereof.

The colouring composition comprises (b) an organic acid. Preferably component (b) comprises an organic acid which is not an aromatic acid. Suitably component (b) comprises an aliphatic organic acid.

Suitable organic acids include acetic acid, tartaric acid, citric acid, glycolic acid, lactic acid, malic acid, maleic acid, succinic acid, malonic acid and 3-hydroxypropanoic acid.

Especially preferred organic acids are polycarboxylic acids.

Preferred organic acids include tartaric acid, succinic acid, citric acid, glycolic acid, lactic acid, malic acid and 3-hydroxypropanoic acid.

Most preferably the organic acid is citric acid.

The organic acid is suitably present in an amount of at least 0.1 wt %, preferably at least 0.5 wt %, more preferably at least 1 wt %.

In some preferred embodiments lower amounts may be included.

The organic acid is suitably present in an amount of up to 20 wt %, suitably up to 15 wt %, preferably up to 10 wt %, more preferably up to 8 wt %, preferably up to 6 wt %, suitably up to 5 wt %, preferably up to 3 wt %.

Most preferably the organic acid is present in an amount of from 0.5 to 5 wt %, preferably from 1 to 3 wt %, more preferably from 1.5 to 2.5 wt %.

Component (b) may comprise a mixture of two or more organic acids, for example two or more aliphatic organic acids. In such embodiments the above amounts refer to the total of all such organic acids present in the composition.

The colouring composition further comprises (c) an alkylene carbonate.

Preferred alkylene carbonates are $C_2$ to $C_6$ alkylene carbonates.

Preferably the alkylene carbonate is selected from propylene carbonate, ethylene carbonate and mixtures thereof.

Preferably the alkylene carbonate is present in an amount of at least 1 wt %, preferably at least 3 wt %, more preferably at least 5 wt %, suitably at least 10 wt %, for example at least 15 wt %.

Preferably the alkylene carbonate may be present in an amount of up to 50 wt %, suitably up to 40 wt %, preferably up to 30 wt %, more preferably up to 25 wt %.

In embodiments in which a mixture of two or more alkylene carbonate compounds are present the above amounts refer to the total of all alkylene carbonate compounds present in the composition.

Suitably alkylene carbonate compounds are present in the composition in a total amount of from 5 to 40 wt %, preferably from 10 to 30 wt %.

Preferably the colouring composition comprises from 0.1 to 40 wt % of propylene carbonate, preferably from 1 to 30 wt %, more preferably from 10 to 30 wt %, for example from 15 to 25 wt %.

The colouring composition further comprises (d) an alcohol.

Suitably component (d) comprises an alcohol which is not an aromatic alcohol. Suitably component (d) comprises an aliphatic alcohol.

Preferred alcohols are water miscible alcohols.

Suitably the alcohol is a monohydric alcohol.

Preferably the alcohol is a $C_1$ to $C_4$ alcohol.

Suitably the alcohol is selected from ethanol, n-propanol, isopropanol, butanol and mixtures thereof.

Preferably the alcohol is isopropanol and/or ethanol.

Most preferably component (d) comprises ethanol and isopropanol.

Preferably isopropanol and ethanol are included in a weight ratio of from 10:1 to 1:10, preferably from 5:1 to 1:5, more preferably from 2:1 to 1:2, for example from 1.5:1 to 1:1.5.

The alcohol is preferably present in an amount of at least 1 wt %, preferably at least 3 wt %, preferably at least 5 wt %, suitably at least 8 wt %.

The alcohol is suitably present in an amount of up to 50 wt %, suitably up to 30 wt %, preferably up to 20 wt %, more preferably up to 15 wt %, preferably up to 12 wt %.

In embodiments in which a mixture of two or more alcohols are present the above amounts refer to the total of all such alcohols present in the composition.

Suitably alcohols are present in the composition in a total amount of from 1 to 40 wt %, preferably from 2 to 30 wt %, for example from 5 to 15 wt %.

Preferably the colouring composition comprises from 1 to 10 wt %; preferably from 2 to 8 wt % ethanol; and from 1 to 10 wt %; preferably from 2 to 8 wt % isopropanol.

The colouring composition further comprises (e) glycerol and/or urea.

In preferred embodiments component (e) comprises glycerol and urea.

Suitably glycerol and urea together comprise at least 1 wt % of the colouring composition, preferably at least 5 wt %, more preferably at least 10 wt %.

Suitably glycerol and urea together comprise up to 50 wt % of the composition, preferably up to 40 wt %, more preferably up to 30 wt %, suitably up to 25 wt %.

Suitably the weight ratio of glycerol to urea is from 20:1 to 1:10, preferably from 10:1 to 1:5, preferably from 5:1 to 1:2, more preferably from 3:1 to 1:1, for example about 2:1.

In some embodiments the composition comprises at least 1 wt % glycerol, preferably at least 3 wt %, more preferably at least 5 wt %, preferably at least 8 wt %.

The composition suitably comprises up to 30 wt % glycerol, preferably up to 20 wt %, suitably up to 15 wt %, for example up to 12 wt %.

In some preferred embodiments the colouring composition comprises at least 0.1 wt % urea, preferably at least 1 wt %, suitably at least 2 wt %, for example at least 3 wt %

Urea may be present in an amount of up to 20 wt %, preferably up to 10 wt %, for example up to 8 wt %.

In some preferred embodiments the colouring composition comprises 1 to 10 wt % urea and 5 to 20 wt % glycerol.

In some embodiments the composition further comprises a thickener.

Any suitable thickener may be used.

Suitable thickeners include those mentioned on the INCI list.

Preferred thickeners are water soluble thickeners.

Suitable thickeners include natural thickeners and synthetic compounds.

Suitable synthetic thickeners include, for example, polyacrylate thickeners.

Preferred thickeners are natural thickeners, especially polysaccharide based thickeners.

Suitable polysaccharide based thickeners include xanthan gum, guar gum, acacia gum, alginates and cellulose-based thickeners.

One especially preferred thickener for use herein is sold under the trade mark Solagum AX and comprises xanthan gum and acacia gum.

The thickener is suitably present in an amount of at least 0.1 wt %, preferably at least 0.25 wt %, preferably at least 0.5 wt %, suitably at least 0.75 wt %, preferably at least 1 wt %.

The thickener is suitably present in an amount of up to 20 wt %, suitably up to 15 wt %, preferably up to 10 wt %, more preferably up to 5 wt %, preferably up to 3 wt %.

The colouring composition may comprise a mixture of two or more thickeners. In such embodiments the above amounts refer to the total of all thickeners present in the composition.

Suitably thickeners are present in the composition in a total amount of from 0.1 to 5 wt %, suitably from 1 to 3 wt %.

In some preferred embodiments the colouring composition further comprises a surfactant.

Any suitable surfactant may be used including anionic, cationic, non-ionic or zwitterionic surfactants.

Preferred surfactants are non-ionic surfactants, especially alkoxylated compounds.

Preferably the surfactant is an alkoxylated silicone surfactant.

One especially preferred surfactant for use herein is PEG-12 dimethicone.

The surfactant is preferably present in an amount of from 0.01 to 10 wt %, preferably from 0.1 to 5 wt %, for example from 1 to 3 wt %.

The colouring composition may comprise a mixture of two or more surfactants.

In such embodiments the above amounts refer to the total of all surfactants present in the composition.

Preferably the colouring composition comprises citric acid.

Preferably the composition comprises 0.1 to 10 wt %, preferably 1 to 3 wt % citric acid.

Preferably the composition comprises propylene carbonate.

Preferably the composition comprises 1 to 30 wt %, preferably 15 to 25 wt % propylene carbonate.

Preferably the composition comprises ethanol.

Preferably the composition comprises 0.1 to 20 wt %, preferably 1 to 10 wt % ethanol.

Preferably the composition comprises isopropanol.

Preferably the composition comprises 0.1 to 20 wt %, preferably 1 to 10 wt % isopropanol.

Preferably the composition comprises glycerol.

Preferably the composition comprises 0.1 to 20 wt %, preferably 5 to 15 wt % glycerol.

Preferably the composition comprises urea.

Preferably the composition comprises 0.1 to 10 wt %, preferably 2 to 8 wt % urea.

The colouring composition preferably comprises less than 0.1 wt % thiourea. Preferably the colouring composition does not comprise thiourea.

Preferably the composition of the present invention comprises less than 1 wt % thiol, preferably less than 0.1 wt %, more preferably less than 0.01 wt %, preferably less than 0.001 wt %.

The colouring composition preferably does not comprise a thiol.

Apart from the dye compounds, the composition of the present invention preferably comprises less than 1 wt % of sulfur-containing compounds, preferably less than 0.1 wt %, more preferably less 0.01 wt %, preferably less than 0.001 wt %.

The colouring composition preferably does not contain any sulfur-containing compounds other than the dye compounds.

Preferably the colouring composition of the present invention comprises less than 1 wt % pyrrolidone compounds, preferably less than 0.1 wt %, more preferably less than 0.01 wt %, preferably less than 0.001 wt %.

Preferably the composition of the present invention does not comprise any pyrrolidone compounds.

Preferably the colouring composition of the present invention comprises less than 1 wt % peroxide compounds, preferably less than 0.01 wt %, more preferably less than 0.001 wt %, preferably less than 0.0001 wt %.

Preferably the composition does not comprise any peroxide compounds.

Preferably the composition of the present invention comprises less than 1 wt % lactones, preferably less than 0.01 wt %, more preferably less than 0.001 wt %, preferably less than 0.0001 wt %.

Preferably the composition does not comprise any lactones.

Suitably the composition of the present invention comprises less than 1 wt % ammonia, preferably less than 0.01 wt %, more preferably less than 0.001 wt %, preferably less than 0.0001 wt %.

Preferably the composition does not comprise any ammonia.

Suitably the composition of the present invention comprises less than 1 wt % pigments, preferably less than 0.01 wt %, more preferably less than 0.001 wt %, preferably less than 0.0001 wt %.

Preferably the composition does not comprise any pigments.

Suitably the composition of the present invention comprises less than 1 wt % iron compounds, preferably less than 0.01 wt %, more preferably less than 0.001 wt %, preferably less than 0.0001 wt %.

Preferably the composition does not comprise any iron compounds.

Suitably the composition of the present invention comprises less than 1 wt % transition metal compounds, preferably less than 0.01 wt %, more preferably less than 0.001 wt %, preferably less than 0.0001 wt %.

Preferably the composition does not comprise any transition metal compounds.

In some preferred embodiments the colouring composition comprises:
- a) one or more dye compounds selected from Acid Yellow 23, Food Red 17, Acid Blue 9 and Acid Green 25;
- b) an organic acid;
- c) propylene and/or ethylene carbonate;
- d) ethanol and/or isopropanol; and
- e) glycerol and/or urea.

In a preferred embodiment the colouring composition comprises:
- a) one or more dye compounds selected from Acid Yellow 23, Food Red 17, Acid Blue 9 and Acid Green 25;
- b) citric acid;
- c) propylene carbonate;
- d) ethanol and isopropanol; and
- e) glycerol and urea.

In some especially preferred embodiments the colouring composition comprises:
- a) 0.1 to 5 wt % of one or more dye compounds selected from Acid Yellow 23, Food Red 17, Acid Blue 9 and Acid Green 25;
- b) 0.1 to 10 wt % citric acid;
- c) 10 to 30 wt % propylene carbonate;
- d) 5 to 15 wt % total ethanol and isopropanol; and
- e) 5 to 30 wt % total glycerol and urea.

In some especially preferred embodiments the colouring composition comprises:
- a) 0.5 to 2 wt % of one or more dye compounds selected from Acid Yellow 23, Food Red 17, Acid Blue 9 and Acid Green 25;
- b) 1 to 4 wt % citric acid;
- c) 15 to 25 wt % propylene carbonate;
- d) 1 to 10 wt % ethanol and 1 to 10 wt % isopropanol; and
- e) 1 to 10 wt % urea and 5 to 15 wt % glycerol.

In some especially preferred embodiments the colouring composition comprises:
- a) 0.5 to 2 wt % of one or more dye compounds selected from Acid Yellow 23, Food Red 17, Acid Blue 9 and Acid Green 25;
- b) 1 to 4 wt % citric acid;
- c) 15 to 25 wt % propylene carbonate;
- d) 2 to 8 wt % ethanol and 2 to 8 wt % isopropanol; and
- e) 2 to 8 wt % urea and 8 to 12 wt % glycerol.

In some especially preferred embodiments the colouring composition comprises:
- a) 0.5 to 2 wt % of one or more dye compounds selected from Acid Yellow 23, Food Red 17, Acid Blue 9 and Acid Green 25;
- b) 1 to 4 wt % citric acid;
- c) 18 to 22 wt % propylene carbonate;
- d) 3 to 7 wt % ethanol and 3 to 7 wt % isopropanol; and
- e) 3 to 7 wt % urea and 8 to 12 wt % glycerol.

The colouring composition may comprise one or more further ingredients for example colourants, fragrances, emollients, pH adjusting agents, surfactants and chelating agents. The selection of such components is within the competence of the skilled person in the art.

The colouring composition is preferably an aqueous composition. Suitably it comprises at least 5 wt % water, preferably at least 10 wt % water, more preferably at least 20 wt %, suitably at least 30 wt %.

The colouring composition preferably comprises less than 90 wt % water, preferably less than 80 wt % water, suitably less than 75 wt % water, for example less than 70 wt %, for example less than 65 wt % or less than 60 wt %.

Preferably the colouring composition is acidic.

Preferably the colouring composition has a pH of from 1 to 6, suitably from 2 to 5, preferably from 2.5 to 4.5, more preferably from 3 to 4.

The composition may suitably comprise one or more pH adjusting agents. Suitable compounds of this type will be known to the person skilled in the art. Preferred pH adjusting agents include sodium hydroxide and aminomethyl propanol.

In some embodiments the colouring composition may be prepared immediately prior to application to the eyebrows, for example from two or more precursor compositions. Compositions of this type are known to the person skilled in the art and allow components that may interact with each other to be stored separately to increase the shelf life of the product.

However in preferred embodiments the colouring composition is provided as a single ready to use fully formulated composition. Advantageously the colouring composition of the present invention is shelf stable. Suitably it does not chemically or physically degrade on storage under ambient conditions for more than six months.

The colouring composition is suitably in the form of a gel or paste.

It suitably has a consistency that enables it to be stirred. Suitably the composition may be easily applied to the eyebrows but once in position it does not drip or run.

The colouring composition may be applied to the eyebrows by any suitable means.

The composition may suitably be massaged or rubbed onto the eyebrows or brushed onto the eyebrows.

In some embodiments the composition is applied by a brush or other applicator.

The composition may be provided in a pot or tube in which the applicator may be dipped and then used to apply the composition to the eyebrows.

In some embodiments the composition may be provided in a container which includes an applicator, through which it passes, for example a pen-type device.

After application the composition may be spread across the brow using fingers and/or an applicator.

Any composition which is accidentally spread onto the skin around the eyebrows is suitably wiped away.

In some embodiments the method of the present invention is used to colour eyebrows that have been previously dyed and/or bleached. In such embodiments the hair may be damaged.

It has been advantageously found that excellent dyeing can be achieved at ambient temperature.

The colouring composition is preferably contacted with the eyebrows for a period of at least 0.1 minutes, preferably at least 0.5 minutes, more preferably at least 1 minute.

The composition may be contacted with the eyebrows for a period of up to 2 hours, suitably up to 1 hour, preferably up to 30 minutes, for example up to 15 minutes. A contact time of 2 to 10 minutes is especially preferred.

Suitably the method of the first aspect includes a step (ii) of removing the composition from the eyebrow.

At the end of the contact time the composition may be wiped from the eyebrows. This may be carried out using a tissue, cotton pad or other wipe.

In some embodiments the composition may be rinsed away with water or mild soap solution.

According to a third aspect there is provided a kit comprising a composition of the second aspect and means for applying the composition to the eyebrow.

Any suitable means for applying the composition to the eyebrows may be provided, such as is described above.

In some embodiments the kit may comprise a device comprising a reservoir containing the colouring composition and means for applying the composition to the eyebrow. Suitably the reservoir and means for applying the composition to the eyebrow (an application means) are part of the same single device.

Suitably the device comprises a reservoir connected to an application means.

The application means suitably comprises a narrow opening through which the composition can be applied directly onto the eyebrow. In some embodiments a brush or fibres may be provided at the opening to assist with application of the composition.

The kit of the third aspect may further comprise a means for removing the composition from the eyebrows. This may be a wipe, tissue or cotton pad. In some embodiments a rinsing composition may be provided, optionally with means for applying the rinsing solution. Such a rinsing solution would be an aqueous composition comprising mild surfactants, typically non-ionic and/or anionic surfactants.

In some embodiments the kit may further comprise a clean-up solution. This can be used to remove any excess colouring which is unintentionally applied or spilled onto a part of the skin and/or hair which is it not desired to be coloured.

The clean-up solution is preferably an aqueous based system which comprises up to 40 wt % of a water miscible alcohol, for example 5 to 35 wt %, or 10 to 30 wt % ethanol. The clean-up solution typically comprises a mixture of surfactants (preferably non-ionic and/or anionic surfactants), suitably in an amount of up to 10 wt %, preferably 0.1 to 5 wt %. The clean-up solution suitably is preferably alkaline. Suitably it has a pH of more than 8, preferably from 9 to 11.

The kit may further comprise instructions for use.

Suitably eyebrows dyed according to the method of the first aspect of the present invention are dyed evenly and consistently.

Suitably eyebrows dyed according to the present invention have excellent wash fastness.

Suitably eyebrows coloured by the method of the present invention shows substantially no fading after 5 washes of the face, preferably after 10 washes, suitably after 15 washes, more preferably after 20 washes of the face.

The method of the second aspect of the present invention may be regarded as a method of "permanently" dyeing eyebrows.

The colouring composition and method have been found to provide excellent dyeing of eyebrows. In particular eyebrows coloured according to the invention are dyed evenly and deep dyeings are achieved even when colouring eyebrows that have been previously bleached and/or dyed.

According to a fourth aspect of the present invention there is provided the use of a composition comprising:
(a) one or more dye compounds selected from Acid Yellow 23, Food Red 17, Acid Blue 9 and Acid Green 25;
(b) an organic acid;
(c) an alkylene carbonate;
(d) an alcohol; and
(e) glycerol and/or urea.
to colour eyebrows.

Preferred features of the fourth aspect are as defined in relation to the first and/or second aspects.

Suitably the use of the fourth aspect provides an even and consistent colour.

Suitably the use of the fourth aspect provides a colour having excellent wash fastness.

The present invention offers significant advantages over methods of dyeing eyebrows of the prior art.

The composition is easy to apply and has a fast development time. It is flexible to use because an operator can easily return to any areas of the brows that have been missed and add more product. Advantageously the colouring compositions of the present invention do not cause staining of the skin.

The present invention has also been found to provide longer lasting dyeing of the brow hairs than methods of the prior art.

A further advantage of the compositions of the present invention is that they provide a consistent colour even after long term storage.

The applicant found that some formulations could deteriorate during storage and/or during the dyeing process leading to a change in the colour of the composition. This effect can be prevented by the inclusion of glycerol and/or urea in the composition.

According to a fifth aspect of the present invention there is provided the use of glycerol and/or urea to improve the stability of an eyebrow colouring composition comprising one or more dye compounds selected from Acid Yellow 23, Food Red 17, Acid Blue 9 and Acid Green 25; an organic acid; an alcohol and an alkylene carbonate.

Preferred features of the colouring composition of the fifth aspect are as defined in relation to the first and second aspects.

The invention will now be further described with reference to the following non-limiting examples:

EXAMPLE 1

Eyebrow colouring compositions were prepared comprising the components listed in table 1.

The compositions were contacted with European natural white hair for 10 minutes at 30° C. on foil open to the air before rinsing and drying.

The stability of the compositions was compared by observing the colour of the composition after 10 minutes, 2 hours and 3 days. The initial and desired colour was brown. The results are also shown in table 1.

TABLE 1

| Composition | 1 | 2 | 3 | 4 | 5 |
|---|---|---|---|---|---|
| Ingredients (wt %) | | | | | |
| citric acid | 2 | 2 | 2 | 2 | 2 |
| propylene carbonate | 20 | 20 | 20 | 20 | 20 |
| ethanol | 5 | 5 | 5 | 5 | 5 |
| isopropanol | 5 | 5 | 5 | 5 | 5 |
| Solagum AX (RTM) | 2.25 | 2.25 | 2.25 | 2.25 | 2.25 |
| Food Red 17 | 0.3 | 0.3 | 0.3 | 0.3 | 0.3 |
| Acid Green 25 | 0.1 | 0.1 | 0.1 | 0.1 | 0.1 |
| Acid Blue 9 | 0.03 | 0.03 | 0.03 | 0.03 | 0.03 |
| Acid Yellow 23 | 0.03 | 0.03 | 0.03 | 0.03 | 0.03 |
| Sodium hydroxide | to pH 3.5 | to pH 3.5 | to pH 3.5 | to pH 3.5 | to pH 3.5 |
| urea | — | — | — | — | 5 |
| glycerol | — | — | — | 10 | 10 |
| propylene glycol | — | 10 | — | — | — |
| dipropylene glycol | — | — | 10 | — | — |
| Performance | | | | | |
| Dyeing performance | poor | poor | poor | good | excellent |
| Colour after 10 minutes | green | green | green | brown | brown |
| Colour after 2 hours | | | | brown | brown |
| Colour after 3 days | | | | green | brown |

EXAMPLE 2

Composition 5 of example 1 was applied to eyebrows using an angled brush. The form of the composition allowed it to be precisely applied, with a focus on areas of the brows that are missing brow hairs.

After 2 to 10 minutes (depending on depth required) the composition was wiped off the brows with a wet cotton wool pad or wipe. The eyebrows can then be shaped as required.

The result was excellent dyeing of the eyebrow without skin staining.

The invention claimed is:

1. A method of colouring an eyebrow, the method comprising:
   (i) applying to the eyebrow a colouring composition comprising:
      (a) 0.5 to 2 wt % of one or more dye compounds selected from Acid Yellow 23, Food Red 17, Acid Blue 9 and Acid Green 25;
      (b) 1 to 4 wt % citric acid;
      (c) 15 to 25 wt % propylene carbonate;
      (d) 1 to 10 wt % ethanol and 1 to 10 wt % isopropanol; and
      (e) 5 to 15 wt % glycerol and 1 to 10 wt % urea.

2. A colouring composition for colouring eyebrows comprising:
   (a) 0.5 to 2 wt % of one or more dye compounds selected from Acid Yellow 23, Food Red 17, Acid Blue 9 and Acid Green 25;
   (b) 1 to 4 wt % citric acid;
   (c) 15 to 25 wt % propylene carbonate;
   (d) 1 to 10 wt % ethanol and 1 to 10 wt % isopropanol; and
   (e) 5 to 15 wt % glycerol and 1 to 10 wt % urea.

3. A method according to claim 1 wherein the colouring composition further comprises an alkoxylated silicone surfactant.

4. A method according to claim 1 wherein the colouring composition comprises less than 70 wt % water.

5. A method according to claim 1 wherein the colouring composition has a pH of from 2 to 5.

6. A method according to claim 1 which does not stain the skin.

7. A kit comprising the composition of claim 2 and means for applying the composition to the eyebrows.

8. A kit according to claim 7 wherein which comprises a device comprising a reservoir connected to an application means.

* * * * *